(12) United States Patent
Pajotin et al.

(10) Patent No.: US 6,368,541 B1
(45) Date of Patent: *Apr. 9, 2002

(54) METHOD OF MANUFACTURING A CURVED PROSTHETIC MESH

(75) Inventors: Docteur Philippe Pajotin, Cholet (FR); John W. Coddaire, Chelmsford; Fred D. Herzog, Westford, both of MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/346,791

(22) Filed: Jul. 2, 1999

Related U.S. Application Data

(62) Division of application No. 08/686,151, filed on Jul. 24, 1996, now Pat. No. 5,954,767, which is a continuation of application No. 08/615,273, filed on Mar. 13, 1996, now abandoned.

(30) Foreign Application Priority Data

Sep. 13, 1993 (FR) ............................................. 93 10857
Sep. 13, 1994 (WO) ............................... PCT/US94/10297

(51) Int. Cl.⁷ ......................... B29C 71/02; B29C 43/52; B29C 35/02; B29C 35/16; B29C 33/20
(52) U.S. Cl. ..................... 264/324; 264/345; 264/346; 264/348; 425/384; 425/395; 425/446; 425/DIG. 48
(58) Field of Search ............................... 264/235, 237, 264/324, 346, 348, 234, 345; 425/384, 395, 446, DIG. 48

(56) References Cited

U.S. PATENT DOCUMENTS

| | | | |
|---|---|---|---|
| 2,671,444 A | 3/1954 | Pease | 606/151 |
| 3,988,411 A | 10/1976 | Capozza | 264/184 |
| 4,345,414 A * | 8/1982 | Bornat et al. | 53/425 |
| 4,403,604 A | 9/1983 | Wilkinson | 600/37 |
| 4,441,215 A | 4/1984 | Kaster | 623/1.53 |
| 4,555,378 A * | 11/1985 | Martin et al. | 264/292 |
| 4,573,999 A | 3/1986 | Netto | 623/7 |
| 4,693,720 A | 9/1987 | Scharnberg | 623/23.72 |
| 4,728,328 A | 3/1988 | Hughes | 623/23.69 |
| 4,841,948 A | 6/1989 | Bauer | 128/897 |
| 5,061,277 A * | 10/1991 | Carpentier et al. | 623/2 |
| 5,146,933 A | 9/1992 | Boyd | 128/899 |
| 5,258,000 A | 11/1993 | Gianturco | 606/151 |
| 5,292,328 A * | 3/1994 | Hain et al. | 606/151 |

(List continued on next page.)

FOREIGN PATENT DOCUMENTS

| | | |
|---|---|---|
| AU | 593 267 B | 1/1988 |
| DE | 892 663 C | 10/1953 |
| DE | 40 13 447 C1 | 2/1992 |
| DE | 92 12 261 U | 11/1993 |
| FR | 2 682 284 A1 | 4/1993 |
| GB | 2 226 762 A | 7/1990 |
| WO | WO 92/13500 | 8/1992 |

*Primary Examiner*—Jan H. Silbaugh
*Assistant Examiner*—Michael I. Poe
(74) *Attorney, Agent, or Firm*—Wolf, Greenfield & Sacks, P.C.

(57) ABSTRACT

A method is provided for fabricating an implantable prosthesis for repairing a defect in a muscle and tissue wall, the prosthesis having a first surface which is convex and a second surface which is concave. The method includes steps of providing a first template having a predetermined concave shape; providing a second template having a predetermined convex shape; placing a piece of implantable flexible mesh between the first and second templates; heating the mesh to a predetermined temperature for a predetermined length of time so that the mesh retains the predetermined shape; and removing the mesh from between the first and second templates. In another aspect, a package is provided for storing a resilient, preformed implantable prosthesis having a first surface with a concave shape and a second surface with a convex shape.

19 Claims, 3 Drawing Sheets

U.S. PATENT DOCUMENTS

| | | | |
|---|---|---|---|
| 5,306,296 A | * 4/1994 | Wright et al. | 623/2 |
| 5,356,432 A | 10/1994 | Rutkow et al. | 623/23.72 |
| 5,383,477 A | 1/1995 | DeMatteis | 128/898 |
| 5,593,441 A | 1/1997 | Lichtenstein et al. | 600/37 |
| 5,674,279 A | * 10/1997 | Wright et al. | 623/2 |
| 5,695,525 A | 12/1997 | Mulhauser et al. | 606/151 |
| 5,716,408 A | * 2/1998 | Eldridge et al. | 623/11 |
| 5,725,577 A | 3/1998 | Saxon | 623/23.72 |
| 5,743,917 A | 4/1998 | Saxon | 128/898 |
| 5,766,246 A | 6/1998 | Mulhauser et al. | 606/151 |

* cited by examiner

METHOD OF MANUFACTURING A CURVED PROSTHETIC MESH

This application is a divisional of application Ser. No. 08/686,151, filed Jul. 24, 1996, U.S. Pat. No. 5,954,767, which is a continuation of application Ser. No. 08/615,273, filed Mar. 13, 1996, now abandoned.

BACKGROUND OF THE INVENTION

1. Field of the Invention

The present invention relates to prosthetic meshes and their methods of manufacture.

2. Description of the Related Art

The prior art includes a prosthetic mesh made of an implantable, non-resorbable, flexible material, designed to be implanted for the parietal repair of hernias and eventrations of the abdominal wall. These meshes, which are usually made of implantable polypropylene, preferably have tight mesh openings and are obtained by knitting, welding or weaving. They are supplied to surgeons pre-cut, in the form of a flat element. However, this flat element must be applied to a concave surface by the surgeon. As a result of the difference in conformation, the mesh is difficult to put into position, especially since one of its relatively broad margins has to be slipped between the parietal peritoneum and the abdominopelvic wall. Moreover, as it is being put in place, the mesh folds or wrinkles and is hard to keep in place at the point where many surgeons prefer to attach it. Its inner margin corresponding to the other small side must be slipped between the bladder and the abdominopelvic wall. A straight margin is poorly suited for insertion of the internal edge.

SUMMARY

The invention palliates these disadvantages by means of a mesh which is easier to put in place and which, once in position, has virtually no tendency to shift, without the need for any additional intervention such as fixation, thereby making it possible to reinforce all the weak points of the inguinofemoral region, resulting in a much lower failure rate than heretofore.

According to the invention, the mesh assumes a curved shape of itself.

Due to this natural curvature which is imparted to it during fabrication and which can match the concavity on which it is to be placed, on being put into place by the surgeon the mesh conforms to the anatomic shapes, and it has no tendency to shift because it is not subjected to strain due to its deformation. By preference, the mesh, while being capable of the temporary deformation necessary for it to be put in place, should have a sufficient tendency to resume its initial curved shape, without deviating therefrom, so that it does not fold or wrinkle under the pressure of the viscera. The preferred mesh resumes its approximate original shape after a single temporary deformation. To obtain this effect more easily, it is desirable for the margins of the mesh to be more rigid than the rest of the mesh, for example by fusing of the material marginally over a width of at least 5 mm. The margins are preferably smooth, to keep the mesh from catching as it is being positioned.

To facilitate insertion, it is preferred that the mesh have, not an external side, but a roughly tapered end by which it can be slipped more easily between the parietal peritoneum and the abdominopelvic wall. It is also preferred that its inner margin, the farthest from that end, be incurvated, especially in its outer portion, roughly according to a circle permitting the repositioning of the bladder after the mesh has been put in place.

For optimum fitting of the mesh to the areas requiring reinforcement, the mesh can have a double convexity in two perpendicular planes.

According to one embodiment, this mesh is composed of a part in the form of a spherical cap extending from the inner margin to beyond the location where the strongest reinforcement is desired, prolonged by a conical part which, at its end, defines the outer tip. The radius of the spherical part can be between 80 and 120 mm. The largest dimension of the mesh can be between 120 and 150 mm, while the dimension perpendicular to this largest dimension can be between 70 and 100 mm.

In order for the mesh to fit optimally into the pelvic area, a rounded edge is provided between the spherical cap and the cone on one hand, and a lower part with a large radius of curvature, which has a depression near its center. This depression is designed to be placed opposite the external iliac vessels, while the rounded edge is designed to be placed within the axis of the inguinal ligament.

A further object of the invention is a method of manufacture of a mesh according to the invention, which consists in placing a flat piece of an implantable, non-resorbable, flexible material in a curved template and bringing this piece to a sufficient temperature for a sufficient period of time so that it retains a curved shape, even after cooling, and upon removal from the template.

A final object of the invention is a package for a mesh, which comprises a body in which a cover nests, characterized in that the upper surface of the bottom of the body is derived from a template which, together with a concave part of the same shape provided on the lower surface of the cover, defines a receptacle for the curved mesh.

BRIEF DESCRIPTION OF THE DRAWINGS

In the attached drawings, provided solely as examples.

DETAILED DESCRIPTION

Figure 1:
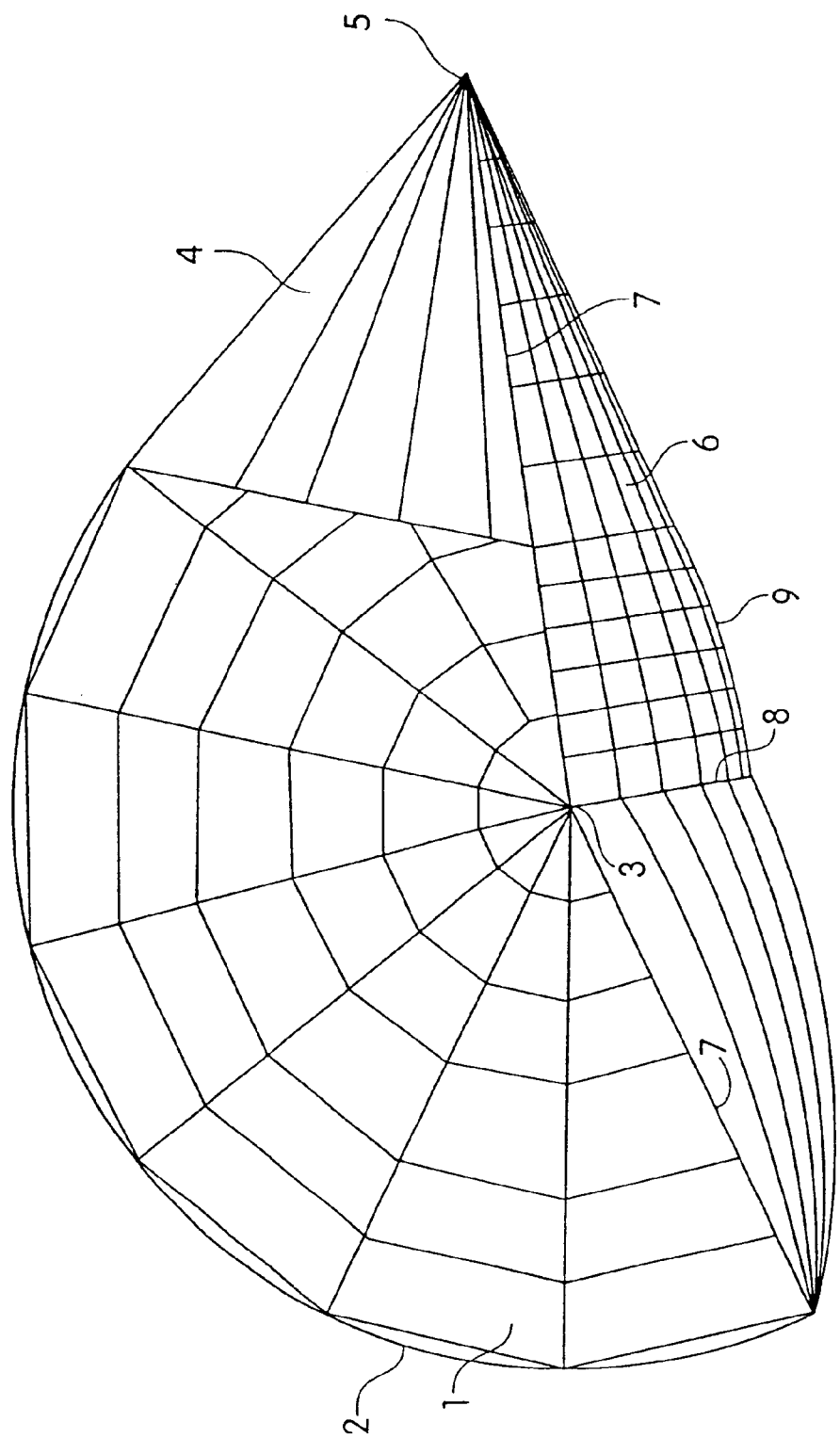
FIG. 1 is a plan view of the mesh according to the invention.
Figure 2:
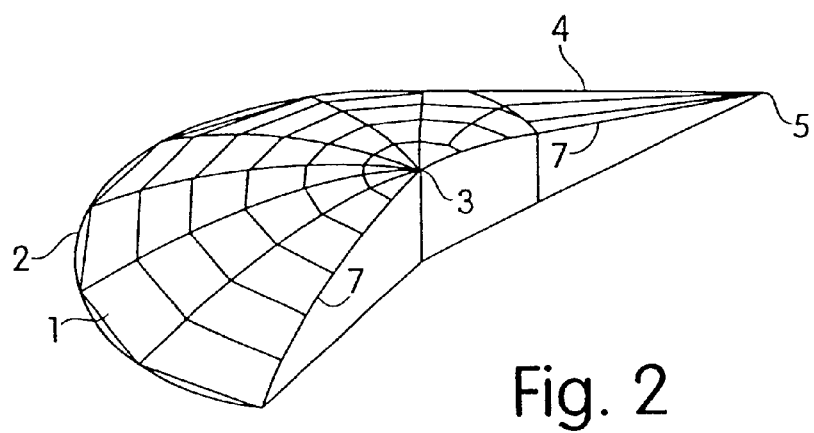
FIG. 2 is a perspective view, partially cut away, of the mesh according to the invention.

The mesh according to the invention is made of knitted polypropylene (MARLEX) cloth; for purposes of clarity, the mesh openings are shown in the drawing as larger than they really are.

The mesh is curved. It comprises a part 1 in the form of a spherical cap extending from the rounded inner margin 2 to beyond the location 3 where the strongest reinforcement is desired. This spherical cap 1 is prolonged by a conical part 4 which defines at its end the outer tip 5. The radius of spherical part 1 is 100 mm, the largest dimension of the mesh from margin 2 to the tip 5 is 130 mm, while the dimension perpendicular to this largest dimension is 85 mm. A lower part 6 is connected both to the spherical cap 1 and to the cone 4 by a rounded edge 7, and a depression 8 is provided beginning at the bottom margin 9 of the lower part, near the median portion.

All the margins of the mesh are smooth and are made more rigid than the rest by fusing the material marginally over a width of 3 mm.

Figure 3:
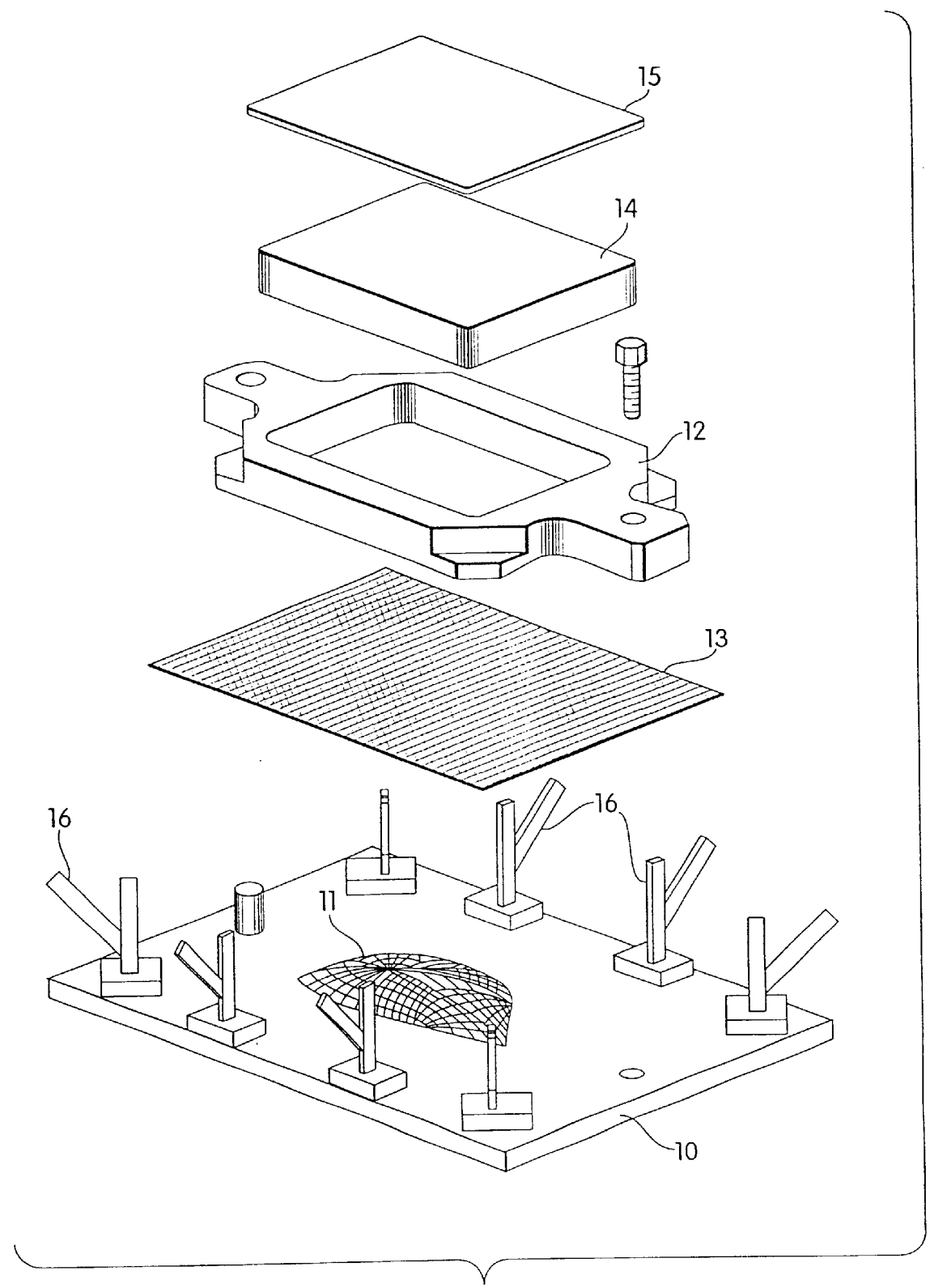
FIG. 3 is an exploded view depicting the method of manufacture of the mesh according to the invention.

In FIG. 3, a template consists of a supporting base 10, from the surface of which is derived a template per se 11 in the shape of the mesh to be obtained, and an aluminum frame 12 designed to clamp the margins of a flat piece of mesh 13 when it is placed on the template 11 after the retaining tabs 16 have been folded down. A silicone frame 14 with a form similar to the template 11 recessed into its inner surface can then be placed on the mesh 13 and held there by an aluminum cover plate 15. Once the flat piece 13 of mesh has been secured in this fashion, it is heated in the template to a temperature of 150° C. for one hour. The template is cooled and the mesh, now curved, is removed.

Figure 4:
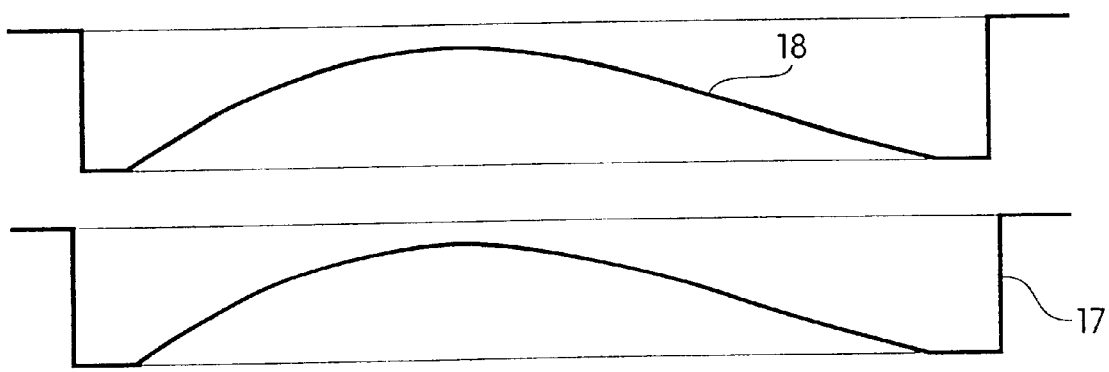
FIG. 4 depicts a package for the mesh.

FIG. 4 depicts a package for the curved mesh. This package consists of a body 17, the upper surface of whose bottom is inwardly convex in the shape of the mesh which it is to hold, and a cover 18 which is inwardly concave in this same shape. When the cover 18 is placed in the body 17, a curved receptacle is defined and the curved mesh is thus held between these two parts in the desired shape.

What is claimed is:

1. A method of fabricating an implantable prosthesis for repairing a defect in a muscle and tissue wall, the prosthesis having a predetermined curved shape with a first surface which is convex and a second surface which is concave, the method comprising steps of:

providing a first template having a predetermined concave curved shape;

providing a second template having a predetermined convex curved shape;

placing a flat piece of implantable flexible mesh between the first and second templates;

heating the mesh to a predetermined temperature for a predetermined length of time between the first and second templates so that the mesh retains the predetermined curved shape to thereby form the prosthesis; and removing the mesh from between the first and second templates.

2. The method recited in claim 1, further comprising a step of:

cooling the mesh prior to the step of removing the mesh.

3. A method for fabricating an implantable prosthesis for repairing a defect in a muscle and tissue wall, the prosthesis including opposing first and second surfaces having a predetermined curved shape, a portion of the first surface having a convex curvature in all directions and a portion of the second surface having a concave curvature in all directions, the method comprising steps of:

providing a first template having a predetermined curved shape, a portion of the first template having a convex curvature in all directions;

providing a second template having a predetermined curved shape, a portion of the second template having a concave curvature in all directions;

placing a flat piece of implantable flexible mesh between the first and second templates;

heating the mesh to a predetermined temperature for a predetermined length of time between the first and second templates so that the mesh retains the predetermined curved shape to thereby form the prosthesis; and removing the mesh from between the first and second templates.

4. The method recited in claim 3, further comprising a step of:

cooling the mesh prior to the step of removing the mesh.

5. A method for fabricating an implantable prosthesis for repairing a defect in a muscle and tissue wall, the prosthesis having a predetermined shape including an inner portion and a peripheral edge surrounding the inner portion, the inner portion having a preformed contoured shape, curved in three dimensions that forms a cavity with an opened end surrounded by the peripheral edge, the inner portion being constructed and arranged to conform to the wall and to minimize shifting of the prosthesis when positioned on the wall, the peripheral edge including at least first and second opposed margins, the first margin having a first curvature and the second margin having a second curvature which is less than the first curvature, the method comprising steps of:

providing a first template having a predetermined shape including a convex inner portion and a curved peripheral edge surrounding the convex inner portion;

providing a second template having a predetermined shape including a concave inner portion and a curved peripheral edge surrounding the concave inner portion;

placing a piece of implantable flexible mesh between the first and second templates;

heating the mesh to a predetermined temperature for a predetermined length of time so that the mesh retains the predetermined shape; and removing the mesh from between the first and second templates.

6. The method recited in claim 5, further comprising a step of:

cooling the mesh prior to the step of removing the mesh.

7. The method recited in claim 5, further comprising a step of forming the peripheral edge stiffer than the inner portion so that the inner portion can regain the preformed contoured shape after being deformed.

8. The method recited in claim 5, further comprising a step of forming the second margin to include a permanent depression intermediate each end of the second margin that is to be placed proximate the iliac vessels when the prosthesis is positioned on the wall to repair an inguinal hernia.

9. A method for fabricating an implantable prosthesis for repairing a defect in a muscle and tissue wall, the wall having an anatomical shape, the prosthesis including a body having an inner portion and a peripheral edge surrounding the inner portion, the inner portion having a preformed shape curved in three dimensions that is adapted to conform to the anatomical shape of the wall, the preformed shape having a spherical portion and a conical portion extending from the spherical portion, the method comprising steps of:

providing a first template having a concave shape with a concave spherical portion and a concave conical portion extending from the concave spherical portion;

providing a second template having a convex shape with a convex spherical portion and a convex conical portion extending from the convex spherical portion;

placing a piece of implantable flexible mesh having a plurality of openings therein between the first and second templates;

heating the mesh to a predetermined temperature for a predetermined length of time so that the mesh retains the anatomical shape;

forming the peripheral edge stiffer than the inner portion so that the inner portion can regain the performed shape after being deformed; and removing the mesh from between the first and second templates.

10. The method recited in claim 9, further comprising a step of:

cooling the mesh prior to the step of removing the mesh.

11. The method recited in claim 9, further comprising a step of forming a permanent depression on the inner portion that is to be placed proximate the iliac vessels when the prosthesis is positioned on the wall to repair an inguinal hernia.

12. A method for fabricating an implantable prosthesis for repairing a defect in a muscle and tissue wall, the prosthesis having a preformed shape constructed and arranged to conform to the wall, the preformed shape including a first curved surface and a second curved surface, the second curved surface having a steeper incline than the first curved surface, the method comprising steps of:

providing a first template having first and second convex surfaces, the second convex surface having a steeper incline than the first convex surface;

providing a second template having first and second concave surfaces which correspond to the first and second convex surfaces of the first template;

placing a piece of implantable flexible mesh between the first and second templates;

heating the mesh to a predetermined temperature for a predetermined length of time so that the mesh retains the shape; and removing the mesh from between the first and second templates.

13. The method recited in claim 12, further comprising a step of:

cooling the mesh prior to the step of removing the mesh.

14. The method recited in claim 12, further comprising a step of forming a peripheral edge about the first and second curved surfaces that is stiffer than the first and second curved surfaces so that the prosthesis can regain the preformed shape after being deformed.

15. The method recited in claim 12, further comprising a step of forming a permanent depression on the second curved surface that is to be placed proximate the iliac vessels when the prosthesis is positioned on the wall to repair an inguinal hernia.

16. A method for fabricating an implantable prosthesis for repairing a defect in a muscle and tissue wall having an anatomical shape, the prosthesis having a preformed shape adapted to conform to the anatomical shape of the wall, the preformed shape including a generally convex outer surface, a generally concave inner surface, a tapered end portion and a curved end portion, the method comprising steps of:

providing a first template having a generally convex shape including a tapered end portion and a curved end portion;

providing a second template having a generally concave shape including a tapered end portion and a curved end portion which corresponds to the first template;

placing a piece of implantable flexible mesh between the first and second templates;

heating the mesh to a predetermined temperature for a predetermined length of time so that the mesh retains the anatomical shape; and removing the mesh from between the first and second templates.

17. The method recited in claim 16, further comprising a step of:

cooling the mesh prior to the step of removing the mesh.

18. The method recited in claim 16, further comprising a step of forming a peripheral edge surrounding the tapered end portion and the curved end portion that is stiffer than the tapered end portion and the curved end portion so that the prosthesis can regain the preformed shape after being deformed.

19. The method recited in claim 16, further comprising a step of forming a permanent depression on the prosthesis that is to be placed proximate the iliac vessels when the prosthesis is positioned of the wall to repair an inguinal hernia.

* * * * *

UNITED STATES PATENT AND TRADEMARK OFFICE
CERTIFICATE OF CORRECTION

| | | |
|---|---|---|
| PATENT NO. | : 6,368,541 B1 | Page 1 of 1 |
| APPLICATION NO. | : 09/346791 | |
| DATED | : April 9, 2002 | |
| INVENTOR(S) | : Docteur Philippe Pajotin et al. | |

It is certified that error appears in the above-identified patent and that said Letters Patent is hereby corrected as shown below:

On the Title Page, Item (62) for Related U.S. Application Data, replace

"08/615,273, filed on Mar. 13, 1996" with -- 08/615,273, filed on Sep. 13, 1994 --.

Signed and Sealed this

Twenty-eighth Day of October, 2008

JON W. DUDAS
*Director of the United States Patent and Trademark Office*